(12) United States Patent
Carter

(10) Patent No.: US 8,697,406 B2
(45) Date of Patent: Apr. 15, 2014

(54) DIRECT CATALYTIC CONVERSION OF SUGARS TO ETHANOL

(76) Inventor: Melvin Keith Carter, Lincoln, CA (US)

( * ) Notice: Subject to any disclaimer, the term of this patent is extended or adjusted under 35 U.S.C. 154(b) by 180 days.

(21) Appl. No.: 12/806,504

(22) Filed: Aug. 16, 2010

(65) Prior Publication Data

US 2012/0041238 A1    Feb. 16, 2012

(51) Int. Cl.
*C12N 1/18* (2006.01)
*C12N 15/74* (2006.01)
*C12P 7/06* (2006.01)
*C12P 7/08* (2006.01)

(52) U.S. Cl.
USPC ...... 435/161; 435/163; 435/254.1; 435/255.2; 435/483

(58) Field of Classification Search
USPC ............................ 435/161, 163, 254.1, 255.2
See application file for complete search history.

*Primary Examiner* — Shawquia Young

(57) ABSTRACT

Sugars comprising the monosaccharides glucose and fructose, and the disaccharides sucrose and mannose are catalytically converted to ethanol in a sulfate fortified acid medium in the presence of transition metal compounds possessing a degree of symmetry. This is not a fermentation process but is a catalytic chemical process where conversion efficiency is improved by saturating the acidic reaction mixture with inorganic sulfate salts to reduce competitive reactions. Ethanol formed during the reaction is removed by distillation facilitating a continuous process.

5 Claims, No Drawings

DIRECT CATALYTIC CONVERSION OF SUGARS TO ETHANOL

BACKGROUND

1. Field of Invention

This invention relates to catalytic chemical conversion of sugars comprising monosaccharides and disaccharides to ethanol at substantial yields in a single process step without fermentation. Specifically, this application discloses rapid, efficient catalytic conversion of sugar materials including sucrose, mannose, glucose, fructose and galactose in an acid medium containing inorganic sulfates comprising alkali metal and alkaline earth sulfates to ethanol employing catalysts based on transition metal complexes possessing a degree of symmetry as described herein.

2. Description of Prior Art

The chemical process industry has grown to maturity based on petroleum feed stocks, a non-renewable resource that may become unavailable in the next 100 years. This planet Earth fosters continual growth of abundant carbohydrate based plants including fruits, vegetables, starches, grain food sources, grasses, shrubs, trees and related natural materials. Trees, corn cobs, support plant stalks, reeds and grasses are subject to catalytic digestion processes converting cellulosic materials to sugar substances where as the present application teaches catalytic conversion of sugars to ethanol. These processes are many times faster and more efficient than fermentation processes. A major industry is blooming in ethanol production and this process is fundamental for efficient catalytic conversion of essentially all sugar materials to ethanol for use as a fuel and starting material in a modern chemical process industry.

Previous methods for production of ethanol include Fischer-Tropsch conversion of syntheses gas and fermentation of sugars. Fermentation of cane and beet sugar, grains and corn, as well as fermentation of sugars produced by acid digestion of wood and related plant cellulose materials constitute the majority of present production processes. Significant effort has been expended to isolate specific enzymes that may be more efficient in the fermentation process and those that might increase conversion efficiency well above ten percent. Ethanol has also been made from ethylene dissolved in sulfuric acid, diluted and isolated by distillation and by heating ethylene with steam at 300° C. and 1000 to 4000 psi pressure using acid or acidic transition metal oxide catalysts but these processes are not efficient in direct production of ethanol.

U.S. Pat. No. 4,415,749, issued Nov. 15, 1983, teaches a process converting methanol and synthesis gas to ethanol and methyl acetate in the vapor phase at 225° C. to 300° C. over zero valent Rh and Fe at 50 psig to 250 psig pressure. U.S. Pat. No. 6,747,067, issued Jun. 8, 2004, presents gasification of cellulose to carbon monoxide and hydrogen for subsequent formation of methanol, ethanol and related products. Neither of these processes start with natural sugars and ethanol is not the primary product. Ligno-cellulose biomass has been converted to sugars, then ethanol using metal salts as discussed in U.S. Pat. No. 6,660,506, issue Dec. 9, 2003. There is also a catalytic process for conversion of sugar alcohols to anhydro-sugar alcohols as disclosed in U.S. Pat. No. 4,409,404, issued Oct. 11, 1983.

U.S. Pat. No. 7,070,967, issued Jul. 4, 2006 teaches application of the flocculent strain *Saccharomyces cerevisae* for conversion of sugar to ethanol by fermentation. U.S. Pat. No. 4,876,196, issued Oct. 24, 1989 discloses a method of continuously producing ethanol from sugar by fermentation using *Zymomonas mobilis* at a pH of from 4.5 to 7 and U.S. Pat. No. 4,797,360, issued Jan. 10, 1989 offers a process for conversion of sucrose to fructose and ethanol by fermentation using *Zymomonas mobilis* and/or the enzyme levansucrase. These fermentation processes are slow and do not teach direct catalytic conversion of essentially any sugar to ethanol.

The present application discloses use of low valent mono-metal, di-metal, tri-metal and/or poly-metal backbone or molecular string type transition metal catalysts, as described in this application, for direct production of ethanol from sugar materials. Catalytic conversion processes are not limited to a single strain or catalyst but are effective using any of a range of catalysts.

SUMMARY OF THE INVENTION

This invention describes a chemical process using selected members of transition metal catalysts possessing a high degree of symmetry in their lower valence states for catalytic conversion of sugar materials to ethanol. This process is rapid and direct in that sugars are placed into solution with the catalytic acid medium at reaction conditions and ethanol is soon distilled out. Fermentation is not required.

It is an object of this invention, therefore, to provide a catalytic process facilitating conversion of sugar materials to ethyl alcohol in a sulfate fortified acid digestion medium. It is another object of this invention to catalytically convert sugar materials to ethanol at normal solvent vapor pressure. It is still another object of this invention to catalytically convert sugar materials to ethanol at elevated temperature. Other objects of this invention will be apparent from the detailed description thereof which follows, and from the claims.

DETAILED DESCRIPTION OF THE INVENTION

A process for catalytic chemical conversion of sugar materials comprising monosaccharides, including glucose and fructose, and disaccharides, including sucrose and mannose, to ethanol is taught. The process for conversion of sugar materials to ethanol uses no fermentation and is conducted in a sulfate fortified acid medium using transition metal compounds, such as $[manganese]_2$, $[iron]_2$ or $[cobalt]_2$ compounds, for which the transition metals and directly attached atoms possess $C_{4v}$, $D_{4h}$ or $D_{2d}$ point group symmetry. These catalysts have been designed based on a formal theory of catalysis, and the catalysts have been produced, and tested to prove their activity. The theory of catalysis rests upon a requirement that a catalyst possess a single metal atom or a molecular string such that transitions from one molecular electronic configuration to another be barrier free so reactants may proceed freely to products as driven by thermodynamic considerations. Catalysts effective for chemical conversion of sugars to ethanol can be made from mono-metal, di-metal, tri-metal and/or poly-metal backbone or molecular string type compounds of the transition metals comprising titanium, vanadium, chromium, manganese, iron, cobalt, nickel, copper, zirconium, niobium, molybdenum, ruthenium, rhodium, palladium, silver, hafnium, tantalum, tungsten, rhenium, osmium, iridium, platinum, gold or combinations thereof. These catalysts are typically made in the absence of oxygen so as to produce compounds wherein the oxidation state of the transition metal is low, typically monovalent, divalent or trivalent. Anions employed for these catalysts comprise fluoride, chloride, bromide, iodide, cyanide, isocyanate, thiocyanate, sulfate, phosphate, oxide, hydroxide, oxalate, acetate, organic chelating agents and/or more complex groups. Mixed transition metal compounds have also been found to be effective catalysts for some chemical conversions.

These catalysts act on glucose, fructose, sucrose, mannose and essentially any sugar type carbohydrate compound to generate free radicals in times believed to be the order of or less than that of a normal molecular vibration. This may be viewed as generation of free radical reactants in equilibrium such that the reaction indicated by the equation $C_6H_{12}O_6 \rightarrow 2CH_3CH_2OH+2CO_2$ may proceed. Water provided in the acid solvent reaction sphere causes hydrolysis of the disaccharides such that catalytic exposure of resulting monosaccharides to monomer, dimer or oligomer transition mthanol and carbon dioxide. Thus, ethanol is the product of catalytic conversion and the carbon dioxide by product is released during the process. Fortifying the acid medium with inorganic sulfates essentially saturates the solvent and reduces the tendency to form known by products.

Catalyst Selection Considerations

A Concepts of Catalysis effort formed a basis for selecting molecular catalysts for specified chemical reactions through computational methods by means of the following six process steps. An acceptable chemical conversion mechanism, involving a single or pair of transition metal atoms, was established for the reactants (step 1). A specific transition metal, such as cobalt, was selected as a possible catalytic site as found in an M or M-M string (step 2), bonded with reactant molecules in essentially a $C_{4v}$, $D_{2d}$ or $D_{4h}$ point group symmetry configuration, and having a computed bonding energy to the associated reactants of $0>E>-60$ kcal/mol (step 3). The first valence state for which the energy values were two-fold degenerate was 2+ in most cases although 1+ is possible (step 4). Sulfate, chloride and other anions may be chosen provided they are chemically compatible with the metal in formation of the catalyst (step 5). An inspection of the designed catalyst should also be conducted to establish compliance with the rule of 18 (or 32) to stabilize the catalyst; thus, compatible ligands may be added to complete the coordination shell (step 6). This same process may be applied for selection of a catalyst using any of the first, second or third row transition metals, however, only those with acceptable negative bonding energies can produce effective catalysts. The approximate relative bonding energy values may be computed using a semi-empirical algorithm or other means. Such a computational method indicated that most of the first row transition metal complexes may be anticipated to produce usable catalysts once the outer coordination shell had been completed with ligands. In general, preliminary energy values computed for transition metal carbohydrate complexes are indicated to produce useable catalysts once bonding ligands have been added.

Catalyst structures commonly including a pair of bonded transition metal atoms require chelating ligands and/or bonding orbital structures that may be different for each metal. The following compounds comprise a limited selection of examples. For the first row transition metals vanadium catalysts comprise vanadium(II) oxide, $(VO)_2$, and $(VF_2)_2$ having V—V bonds and ethylenediamine (EDA) links the metals in $(VCl_2)_2(EDA)_2$, ethanol or other reactants may displace a CO and/or a THF in the compound $[V(THF)_4Cl_2][V(CO)_6]_2$ while $V_2(SO_4)_3$ may also be useful. Chromium catalysts comprise $Cr(O_2CCH_3)_2(HO_2CCH_3)_2$, $Cr_2[CH_3(C_5H_3N)O]_4$, $(CrCl_2)_2 \cdot 2EDA$, $(CrBr_2)_2(EDA)_2$, $[Cr(OH)_2]_2(EDA)_2$ and $Cr_2(O_2CCH_3)_4(H_2O)_2$ where a reactant may displace waters of hydration. Manganese catalysts comprise $[Mn(diethyldithiocarbamate)]_n$, $(MnCl_2)_2(EDA)_2$, $K_2[Mn_2Cl_6(H_2O)_4]$ and $Mn_2(C_5H_8O_2)_4(H_2O)_2$. Iron catalysts comprise $(FeCl_2)_2(EDA)_2$, $(FeBr_2)_2(EDA)_2$ and $Fe_2(SO_4)_2$. Cobalt catalysts comprise $Co_2(C_6H_5O_2)_2(C_6H_6O_2)_2$, $Co_2(C_5H_8O_2)_4(H_2O)_2$, $Co(C_6HSO_2)_2(C_6H_6O_2)_2$, $Co_2(C_6HSO_2)_4$, $Ca_3[Co_2(CN)_{10}]$ $13H_2O$, $[Co(CN)_2]_2K_3Cu(CN)_4$ and $Co_2(SO_4)_2$. Nickel catalysts comprise $Ni_2(C_6H_5N_3C_6H_5)$, $Ni_2Br_2(C_8H_6N_2)$ and $Ni_2S_2(C_2H_2C_6H_5)$. Copper catalysts comprise $[CuO_2CC_6H_5]_4$, $[CuO_2CCH_3]_4$, $(CuCl)_2(EtOH)_4$, $(CuCN)_2(EtOH)_4$ and $K_2Cu_4(\mu_2SC_6H_5)_6$.

Second and third row transition metals are organized in groups or pairs. Zirconium, hafnium, nobelium and tantalum comprise $(ZrCl_2)_2$, $(HfCl_2)_2$, $(HfF_2)_2$, $(NbCl_2)_2$, $(TaCl_2)_2$ and $(TaF_2)_2$. Molybdenum and tungsten catalysts comprise $[Mo(CO)_4Cl_2]_2$, $[W(CO)_4Cl_2]_2$, $[K_4MoCl_6]_2$, $[Mo(CN)_2]_2K_3Cu(CN)_4$, $[W(CN)_2]_2K_3Cu(CN)_4$, $[Mo(Cl)_2]_2K_3Cu(CN)_4$ and $[W(Cl)_2]_2K_3Cu(CN)_4$. Rhenium and technetium catalysts comprise $[Re(CO)_2Cl_2(PR_3)_3]_2$ and $[Tc(CO)_2Cl_2(PR_3)_3]_2$. Platinum, palladium, ruthenium, rhodium, osmium and iridium catalysts comprise $(PtF_2)_2$, $(PdF_2)_2$, $[RuCl_2]_2(EDA)_4$, $[RhCl_2]_2(EDA)_4$, $[Ru(C_8H_6N_2)_2Cl_2]_2$, $[Rh(C_8H_6N_2)_2Cl_2]_2$, $Ru_2(O_2CR)_4Cl$, $Rh_2(O_2CR)_4Cl$, $[PdCl_4(PBu_3)_2]_2$, $[PtCl_4(PBu_3)_2]_2$, $[OsCl_2]_2(EDA)_4$ and $[IrCl_2]_2(EDA)_4$. Silver and gold catalysts comprise $(AgCN)_2K_3Cu(CN)_4$ and $(AuCN)_2K_3Cu(CN)_4$.

A limited number of single transition metal atom catalyst complexes containing four ligands each belong to the required point group symmetry, although typically these compounds form associated molecular pairs. These catalysts comprise $M(II)(C_6HSO_2)_2(C_6H_6O_2)_2$, $M(II)(p-C_6H_5O_2)_2$, $M(II)(C_6H_6NO)_2(C_6H_7NO)_2$ and $M(II)(O_2CCH_3)_2(HO_2CCH_3)_2$ plus possible solvation ligands where M represents titanium, vanadium, chromium, manganese, iron, cobalt, nickel, copper, zirconium, niobium, molybdenum, ruthenium, rhodium, palladium, silver, hafnium, tantalum, tungsten, rhenium, osmium, iridium, platinum or gold. In a limited number of complexes the transition metal atom may be mono-valent or tri-valent.

Description of Catalyst Preparation and Chemical Conversion

Catalyst preparation may be conducted using nitrogen purging and/or nitrogen blanketing to minimize or eliminate air oxidation of the transition metal compounds during preparation. Transition metal catalysts effective for conversion of sugar materials can be produced by combining transition metal salts in their lowest standard oxidation states with other reactants. Thus, such transition metal catalysts can be made by partially reacting transition metal (I or II) chlorides, bromides, sulfates, cyanides or similar compounds with transition metal (I, II or III) compounds and chelates or by forming transition metal compounds in a reduced state by similar means where di-, tri- and/or poly-metal compounds result. A number of $[M(II)sulfate]_2$ catalysts form by simply adding a transition metal (II) salt to an acid sulfate medium. Some alternate examples follow.

EXAMPLE 1

The $Co_2(C_6H_5O_2)_4$ catalyst was prepared in a nitrogen atmosphere by addition of 0.660 gram (6 mmol) of pyrocatechol dissolved in 3.5 mL of nitrogen purged water to 0.7138 gram (3 mmol) of cobalt (II) chloride hexahydrate dissolved in 3 mL of nitrogen purged water with mixing and addition of 2N sodium hydroxide drop wise to attain a pH of 7. An insoluble dark green to black solid product formed. The suspended catalyst was used as prepared.

EXAMPLE 2

The $Co_2(SO_4)_2$ catalyst was prepared in a nitrogen atmosphere by addition of 0.536 gram (2 mmol) of sodium sulfate to 0.498 gram (2 mmol) of cobalt (II) acetate tetrahydrate dispersed in 6 mL of nitrogen purged water with mixing and heating. A soluble colored product solution formed. The dissolved catalyst was isolated for use.

EXAMPLE 3

The $Cr_2(SO_4)_3$ catalyst was prepared in a nitrogen atmosphere by addition of 0.804 grams (3 mmol) of sodium sulfate to 0.533 grams (2 mmol) of chromium (III) chloride hexahydrate dispersed in 5 mL of nitrogen purged water with mixing and heating. A soluble colored product solution formed. The dissolved catalyst was isolated for use.

EXAMPLE 4

The compound $V_2(O_2CCH_3)_4$ was prepared as described by dispersing 1.82 grams of vanadium pentoxide in 10 grams of pure water, dissolving 3.08 grams of ammonium acetate and 4.48 grams of concentrated hydrochloric acid. This liquid was gently purged with nitrogen gas to displace dissolved oxygen and 6.5 grams of zinc dust was added in portions during a 5 minute period. The dispersion changed to a colored solution as the catalyst formed.

Chemical Conversion to Ethanol

Sugar material conversions were conducted in a sulfate fortified dilute sulfuric acid medium by heating sugar materials in an open reactor with a small amount of catalyst to a temperature in the range of 75° C. to 250° C. The final temperature was maintained while the ethanol solution distilled. Fermentation processes were not employed.

EXAMPLE A

A 40 mL glass vial was fit with a short glass wool packed stainless steel, air cooled distillation column. Dissolved in the vial were 4.06 grams of cesium sulfate, 2.09 grams of magnesium sulfate, 0.0068 gram of cobalt sulfate catalyst, 2.06 grams of water and 3.21 grams of sulfuric acid. The vial \was cooled and 1.09 grams of sucrose was dissolved therein. The glass wool insulated vial was heated to approximately 145° C. and 1.8 mL of distillate was collected and analyzed proving 76 percent conversion to ethanol.

EXAMPLE B

A 40 mL glass vial was fit with a short glass wool packed stainless steel, air cooled distillation column. Dissolved in the vial were 4.07 grams of cesium sulfate, 2.10 grams of magnesium sulfate, 0.012 gram of iron(II) sulfate catalyst, 2.07 grams of water and 3.21 grams of sulfuric acid. The vial was cooled and 1.10 grams of sucrose was dissolved therein. The glass wool insulated vial was heated to approximately 136° C. and 1.7 mL of distillate was collected and analyzed proving 64 percent conversion to ethanol.

EXAMPLE C

A 40 mL glass vial was fit with a short glass wool packed stainless steel, air cooled distillation column left open to the air. Dissolved in the vial were 4.07 grams of cesium sulfate, 2.09 grams of magnesium sulfate, 0.0093 gram of manganese sulfate catalyst, 2.11 grams of water and 3.25 grams of sulfuric acid. The vial was cooled and 1.10 grams of sucrose was dissolved therein. The glass wool insulated vial was heated to approximately 136° C. and 1.7 mL of distillate was collected and analyzed proving 71 percent conversion to ethanol.

EXAMPLE D

A 40 mL glass vial was fit with a short glass wool packed stainless steel, air cooled distillation column. Dissolved in the vial were 4.07 grams of cesium sulfate, 2.09 grams of magnesium sulfate, 0.0092 gram of cobalt sulfate catalyst, 2.06 grams of water and 3.22 grams of sulfuric acid. The vial was cooled and 0.99 grams of glucose was dissolved therein. The glass wool insulated vial was heated to approximately 145° C. and 1.8 mL of distillate was collected and analyzed proving 74 percent conversion to ethanol.

EXAMPLE E

A 40 mL glass vial was fit with a short glass wool packed stainless steel, air cooled distillation column. Dissolved in the vial were 1.524 gram of potassium sulfate, 1.063 grams of sodium sulfate, 0.643 gram of lithium sulfate, 0.0110 gram of manganese sulfate and 0.0157 gram of copper sulfate catalysts in 2.073 grams of water and 3.637 grams of sulfuric acid. The vial was cooled and 0.885 gram of fructose was dissolved there in. The glass wool insulated vial was heated to approximately 140° C. and 1.6 mL of distillate was collected and analyzed proving 19 percent conversion to ethanol.

EXAMPLE F

A 40 mL glass vial was fit with a short glass wool packed stainless steel, air cooled distillation column. Dissolved in the vial were 0.718 gram of potassium sulfate, 0.620 gram of lithium sulfate, 2.06 grams of magnesium sulfate, 0.0065 gram of cobalt sulfate catalyst, 2.05 grams of water and 3.22 grams of sulfuric acid. The vial was cooled and 1.06 grams of sucrose was dissolved therein. The glass wool insulated vial was heated to approximately 130° C. and 1.2 mL of distillate was collected.

neutralized and analyzed proving 57 percent conversion to ethanol.

What is claimed is:

1. A Direct catalytic chemical conversion of sugar materials comprising monosaccharides including glucose and fructose, and disaccharides including sucrose and mannose to ethanol in an acid medium without fermentation.

2. A Direct catalytic chemical conversion of sugar materials comprising monosaccharides including glucose and fructose, and disaccharides including sucrose and mannose to ethanol in an acid medium containing 0.1 percent to 80 percent metal sulfates.

3. A direct catalytic chemical conversion of sugar materials comprising monosaccharides including glucose and fructose, and disaccharides including sucrose and mannose to ethanol in an acid medium containing 0.1 percent to 80 percent metal sulfates at 75° C. to 250° C.

4. A direct catalytic chemical conversion of sugar materials comprising monosaccharides including glucose and fructose, and disaccharides including sucrose and mannose to ethanol in an acid medium containing 0.1 percent to 80 percent metal sulfates wherein catalysts possessing a degree of symmetry are formed from transition metal compounds comprising titanium, vanadium, chromium, manganese, iron, cobalt, nickel, copper, zirconium, niobium, molybdenum, ruthenium, rhodium, palladium, silver, hafnium, tantalum, tungsten, rhenium, osmium, iridium, platinum, gold or combinations thereof.

5. A direct catalytic chemical conversion of sugar materials comprising monosaccharides including glucose and fructose, and disaccharides including sucrose and mannose to ethanol in an acid medium containing 0.1 percent to 80 percent metal sulfates, wherein metal sulfates comprises alkali metal and alkaline earth sulfates, at 75° C. to 250° C. wherein catalysts possessing a degree of symmetry are formed from transition metal compounds comprising titanium, vanadium, chromium, manganese, iron, cobalt, nickel, copper, zirconium, niobium, molybdenum, ruthenium, rhodium, palladium, silver, hafnium, tantalum, tungsten, rhenium, osmium, iridium, platinum, gold or combinations thereof.

* * * * *